United States Patent [19]
Waycuilis

[11] Patent Number: 5,861,441
[45] Date of Patent: Jan. 19, 1999

[54] COMBUSTING A HYDROCARBON GAS TO PRODUCE A REFORMED GAS

[75] Inventor: John J. Waycuilis, Cypress, Tex.

[73] Assignee: Marathon Oil Company, Findlay, Ohio

[21] Appl. No.: 800,642

[22] Filed: Feb. 14, 1997

Related U.S. Application Data

[63] Continuation-in-part of Ser. No. 600,565, Feb. 13, 1996, Pat. No. 5,733,941.

[51] Int. Cl.$^6$ .................................................. C07C 27/06
[52] U.S. Cl. ...................... 518/703; 518/704; 252/373; 60/39.12; 60/39.05; 60/39.53
[58] Field of Search .................................... 518/703, 704; 252/373; 60/39.12, 39.05, 39.53

[56] References Cited

U.S. PATENT DOCUMENTS

| | | | |
|---|---|---|---|
| 2,552,308 | 8/1951 | Buchmann et al. | 260/449.6 |
| 2,660,032 | 7/1953 | Rosenthal | 60/39.02 |
| 2,686,195 | 8/1954 | McAdams et al. | 260/449.6 |
| 3,866,411 | 2/1975 | Marion et al. | 60/39.02 |
| 3,868,817 | 3/1975 | Marion et al. | 60/39.02 |
| 3,920,579 | 11/1975 | Slater | 252/373 |
| 3,959,972 | 6/1976 | Rudolf et al. | 60/651 |
| 3,986,349 | 10/1976 | Egan | 60/39.02 |
| 4,074,981 | 2/1978 | Slater | 48/197 R |
| 4,075,831 | 2/1978 | McGann | 60/39.05 |
| 4,092,825 | 6/1978 | Egan | 60/39.02 |
| 4,121,912 | 10/1978 | Barber et al. | 48/197 R |
| 4,132,065 | 1/1979 | McGann | 60/39.02 |
| 4,158,680 | 6/1979 | McGann | 261/149 |
| 4,309,359 | 1/1982 | Pinto | 518/705 |
| 4,338,292 | 7/1982 | Duranleau | 423/656 |
| 4,434,613 | 3/1984 | Stahl et al. | 60/39.07 |
| 4,618,451 | 10/1986 | Gent | 252/373 |
| 4,678,723 | 7/1987 | Wertheim | 429/17 |
| 4,732,092 | 3/1988 | Gould | 110/229 |
| 4,833,170 | 5/1989 | Agee | 518/703 |
| 4,946,477 | 8/1990 | Perka et al. | 48/197 R |
| 4,973,453 | 11/1990 | Agee | 422/190 |
| 5,026,934 | 6/1991 | Bains et al. | 588/314 |
| 5,177,114 | 1/1993 | Van Dijk et al. | 518/703 |
| 5,245,110 | 9/1993 | Van Dijk et al. | 585/946 |
| 5,295,356 | 3/1994 | Billy | 62/20 |
| 5,472,986 | 12/1995 | van Dijk | 518/705 |

FOREIGN PATENT DOCUMENTS

| | | |
|---|---|---|
| 0 497 425 A1 | 8/1992 | European Pat. Off. . |
| 4-364142 | 12/1992 | Japan . |

OTHER PUBLICATIONS

"The Syntroleum Process" promotional flier, Aug. ,1994.
Hedden, K., et al., "A New Concept for the Production of Liquid Hydrocarbons from Natural Gas in Remote Areas", Oil Gas—European Magazine, Mar. 1994, pp. 42–44.

*Primary Examiner*—Gary Geist
*Assistant Examiner*—Sreeni Padmanabhan
*Attorney, Agent, or Firm*—Jack L. Hummel; Jack E. Ebel

[57] ABSTRACT

A system and process are provided for converting a hydrocarbon gas to a reformed gas containing hydrogen and carbon monoxide. In accordance with a first embodiment, the system includes a primary combustor, compressor and power turbine. The process is practiced by compressing a feed air in the primary compressor to produce a primary air. The primary air is fed with a primary hydrocarbon gas to the primary combustor, producing a reformed gas that drives the primary power turbine. The primary power turbine is linked to the primary compressor, compressing the feed air in an energy self-sufficient manner. In a second embodiment, the system of the first embodiment further includes a secondary combustor, compressor and power turbine. The process is practiced in the same manner as the first embodiment, producing the reformed gas and driving the primary power turbine and compressor. A portion of the primary air is also fed with a secondary hydrocarbon gas to the secondary combustor, producing an off-gas that drives the secondary power turbine and compressor to compress a gas in an energy self-sufficient manner. In a third embodiment, the system is substantially the same as the second embodiment, but reconfigures the compressors and power turbines and further includes an auxiliary secondary power turbine. The process is practiced in the same manner as the first embodiment, producing the reformed gas and driving the primary power turbine and compressor. The off-gas is produced in the same manner as the second embodiment to drive the secondary power turbine, but the secondary power turbine drives an auxiliary primary compressor, compressing the feed air ahead of the primary compressor in an energy self-sufficient manner. The off-gas further drives the auxiliary secondary power turbine to provide additional power for alternate power users.

31 Claims, 3 Drawing Sheets

COMBUSTING A HYDROCARBON GAS TO PRODUCE A REFORMED GAS

This is a continuation-in-part application of application Ser. No. 08/600,565 filed on Feb. 13, 1996, now U.S. Pat. No. 5,733,941.

BACKGROUND OF THE INVENTION

1. Technical Field

The present invention relates generally to a system and process for converting a hydrocarbon gas to a hydrogen-containing gas and, more particularly, to a system and process for combusting a hydrocarbon gas with air to produce a reformed gas containing hydrogen and carbon monoxide.

2. Background Information

A need has long existed for converting available carbonaceous materials to intermediates that can subsequently be converted to scarce, but useful, hydrocarbon products such as liquid hydrocarbon fuels, petrochemicals and the like. For example, coal is one such carbonaceous material that is readily available in some locales. U.S. Pat. No. 3,986,349 teaches a process for gasifying coal to an intermediate synthesis gas that can subsequently be hydrogenated to provide a valuable liquid hydrocarbon fuel. The fuel is used to generate power by relatively clean combustion in an open-cycle gas turbine.

Natural gas is another carbonaceous material that is plentiful in many regions, yet uneconomical to develop because of the lack of local markets for the gas or the high cost of transporting the gas to alternate markets. One solution is to produce the natural gas and convert it in the field to a more utilitarian liquid hydrocarbon fuel or other liquid product. The conversion product can be used locally or cost-effectively transported to alternate markets. Processes for converting light hydrocarbon gases, such as natural gas, to heavier hydrocarbon liquids are generally known in the prior art. Such processes typically involve the "indirect" conversion of methane to synthetic paraffinic hydrocarbon compounds, wherein methane is first converted to an intermediate synthesis gas containing hydrogen and carbon monoxide. The resulting synthesis gas is then converted to liquid synthetic paraffinic hydrocarbon compounds via a Fischer-Tropsch reaction. Unconverted synthesis gas remaining in the process tail gas after the Fischer-Tropsch reaction is usually catalytically reconverted to methane via a methanation reaction and recycled to the process inlet to increase the overall conversion efficiency of the process.

Conversion of methane to a synthesis gas is often performed by high-temperature steam reforming, wherein methane and steam are reacted endothermically over a catalyst contained within a plurality of externally-heated tubes mounted in a large fired furnace. Alternatively, methane is converted to a synthesis gas via partial oxidation, wherein the methane is exothermically reacted with purified oxygen. Partial oxidation using purified oxygen requires an oxygen separation plant having substantial compression capacity and correspondingly having substantial power requirements. Production of the synthesis gas via either of the above-recited means accounts for a major portion of the total capital cost of a plant converting methane to paraffinic hydrocarbons.

Autothermal reforming is a lower cost means of converting methane to a synthesis gas. Autothermal reforming employs a combination of partial oxidation and steam reforming. The heat required to activate the endothermic steam reforming reaction is obtained from the exothermic partial oxidation reaction. Unlike the above-recited partial oxidation reaction, however, air is used as the source of oxygen for the partial oxidation reaction. In addition, the synthesis gas produced by autothermal reforming contains substantial quantities of nitrogen from the inlet air. Consequently, it is not possible to recycle the unconverted components contained in the process tail gas without undesirably accumulating an excess of nitrogen within the process. Production of a nitrogen-diluted synthesis gas via autothermal reforming or partial oxidation using air followed by conversion of the synthesis gas via a Fischer-Tropsch reaction as disclosed in U.S. Pat. Nos. 2,552,308 and 2,686,195 is, nevertheless, a useful means for obtaining synthetic hydrocarbon liquid products from methane.

U.S. Pat. No. 4,833,170 discloses another example of autothermal reforming, wherein a gaseous light hydrocarbon is reacted with air in the presence of recycled carbon dioxide and steam to produce a synthesis gas. The synthesis gas is reacted in the presence of a hydrocarbon synthesis catalyst containing cobalt to form a residue gas stream and a liquid stream comprising heavier hydrocarbons and water. The heavier hydrocarbons are separated from the water and recovered as product. The residue gas is catalytically combusted with additional air to form carbon dioxide and nitrogen which are separated. At least a portion of the carbon dioxide is recycled to the autothermal reforming step.

Prior art hydrocarbon gas conversion processes may be adequate for converting hydrocarbon gases to reformed gases, such as synthesis gas, having utility as intermediates in the production of desirable end products. Nevertheless, such processes have not been found to be entirely cost effective due to significant capital equipment and energy costs attributable to compression of the inlet air. The power required to compress the inlet air represents the majority of the mechanical power required to operate the process, yet much of this power is essentially lost as unrecovered pressure energy in the intermediate reformed gas or off-gas from the process. In addition, significant chemical fuel energy in the form of unconverted compounds and unrecovered products is frequently retained in downstream residue gases. The generally highly dilute nature and low heating value of downstream residue gas inhibits efficient recovery of the fuel energy therefrom. As a result the fuel energy is oftentimes discarded or recovered only with extreme difficulty and expense.

Another drawback experienced with prior art hydrocarbon gas conversion processes, and in particular with autothermal reforming or partial oxidation, is the limited yields of desirable intermediates resulting therefrom. Although the autothermal reforming or partial oxidation reactions approach equilibrium at high temperatures, a significant degree of reverse reaction occurs during the subsequent cooling/quenching step diminishing the net yield of intermediates. Thus, it is apparent that a need exists for a more effective hydrocarbon gas conversion process overcoming the above-described drawbacks of prior art processes.

Accordingly, it is an object of the present invention to provide an effective process for converting a hydrocarbon gas to a reformed hydrogen-containing gas. It is also an object of the present invention to provide an effective system of process equipment for converting a hydrocarbon gas to a reformed hydrogen-containing gas. More particularly, it is an object of the present invention to provide such a hydrocarbon gas conversion system and process having substantially reduced power requirements. It is another object of the present invention to provide such a hydrocarbon gas conversion system and process having substantially reduced capital equipment costs. It is yet another object of the present invention to provide such a hydrocarbon gas conversion system and process effectively utilizing the pressure energy of an off-gas and/or the fuel energy of a downstream residue gas. It is a further object of the present invention to provide such a hydrocarbon gas conversion system and process having improved yields of desirable products. These objects and others are achieved in accordance with the invention described hereafter.

SUMMARY OF THE INVENTION

The present invention is a system and a process for converting a hydrocarbon gas to a reformed hydrogen-containing gas. In a first embodiment of the invention, a first system is provided to perform a first hydrocarbon gas conversion process. The first system includes a single turbine/compressor set, having a primary power turbine and a primary compressor, and a primary combustor, having a combustion zone and a reforming zone. The first process is performed by initially providing a feed to the first system comprising a feed air and a primary hydrocarbon gas divisible into a first portion and a second portion. The feed air is compressed in the primary compressor to produce a primary air divisible into a substantially larger first portion and a substantially smaller second portion. The first portion of primary air is fed with the first portion of primary hydrocarbon gas, and optionally water or steam, to the combustion zone of the primary combustor such that a near-stoichiometric ratio of primary air to primary hydrocarbon gas is achieved in the combustion zone. The primary air and primary hydrocarbon gas, optionally in the presence of water or steam, are combusted in the combustion zone to produce a primary combustion gas.

The primary combustion gas flows downstream in the primary combustor to the reforming zone where it combines with the second portion of primary hydrocarbon gas injected into the primary combustor downstream of the combustion zone. The mixture of the primary combustion gas and the second portion of primary hydrocarbon gas undergo endothermic reforming reactions in the reforming zone that cool the mixture and produce a reformed gas containing hydrogen and carbon monoxide.

Although the overall ratio of primary air to primary hydrocarbon gas fed to the primary combustor is substoichiometric, by maintaining a near-stoichiometirc ratio of primary air to primary hydrocarbon gas in the combustion zone, an ignitable and stable self-sustaining combustion reaction is maintained within the combustion zone without the formation of soot. Feeding water or steam to the combustion zone, desirably increases the ratio of hydrogen to carbon monoxide in the ensuing reformed gas, while diluting and cooling the primary combustion gas and suppressing the formation of soot in the reforming zone.

The reformed gas exits the reforming zone of the primary combustor and is very rapidly expanded across the primary power turbine. The rapid expansion and resultant cooling of the reformed gas effectively quenches the reforming reaction, providing a high yield of desirable hydrogen and carbon monoxide in the reformed gas. Expanding the reformed gas drives the primary power turbine, which is connected by a primary shaft to the primary compressor, thereby driving the primary compressor. The reformed gas is then withdrawn from the system for subsequent uses as desired. The second portion of primary air is bled off from the system to balance the thrust of the primary shaft and may be utilized for other applications external to the system.

In a second embodiment of the invention, an alternate second system is provided to perform an alternate second hydrocarbon gas conversion process having substantially greater throughputs than the first process. The second system includes substantially the same components as the first system operating in substantially the same manner as the first process. The second system, however, further includes a second turbine/compressor set, having a secondary power turbine and a secondary compressor, and a secondary combustor, having a flame zone and a burn-out zone. The additional components are provided to compress the reformed gas utilizing the fuel value of an available secondary hydrocarbon gas in a manner described hereafter. The second process is initially performed by providing a feed to the second system comprising a feed air and a primary hydrocarbon gas divisible into a first portion and a second portion. The feed air is compressed in the primary compressor to produce a primary air divisible into a first portion and a second portion. The first portion of primary air is fed with the first portion of primary hydrocarbon gas, and optionally water or steam, to the combustion zone of the primary combustor, producing a primary combustion gas therein. The primary combustion gas is reacted with the second portion of primary hydrocarbon gas in the reforming zone of the primary combustor to produce a reformed gas that is rapidly expanded across the primary power turbine, thereby driving the primary power turbine and correspondingly driving the primary compressor.

In distinction to the first process, the second portion of primary air is retained within the second system, wherein it is preheated by heat exchange with the reformed gas exiting the primary turbine to form a secondary air that is divided into a first portion and a second portion. The feed to the system further comprises a secondary hydrocarbon gas, preferably a low heating value waste gas from an external source, that is preheated by heat exchange with the reformed gas downstream of the air preheating step. The preheated secondary hydrocarbon gas is fed with the first portion of secondary air to the flame zone of the secondary combustor and combusted therein to produce a secondary combustion gas. The second portion of secondary air is fed with the secondary combustion gas, and optionally water or steam, to the burn-out zone of the secondary combustor to further oxidize residual hydrocarbons, hydrogen, carbon monoxide and other combustibles in the secondary combustion gas to carbon dioxide and water. The secondary combustion gas is also diluted and cooled in the burn-out zone, suppressing the formation of oxides of nitrogen in the off-gas exiting the secondary combustor. The resulting off-gas is expanded across the secondary power turbine, thereby driving the secondary power turbine and correspondingly driving the secondary compressor by means of a secondary shaft connected thereto before discharging the off-gas from the system.

After cooling the reformed gas by heat exchange with the second portion of primary air and the secondary hydrocarbon gas, the reformed gas is further cooled to near ambient temperature in a conventional cooling means and conveyed to a water separator where condensed water is removed from the reformed gas and discharged from the system. The reformed gas is then compressed in the secondary compressor and withdrawn from the system at a relatively high pressure for subsequent uses as desired.

In a third embodiment of the invention, an alternate third system is provided to perform an alternate third hydrocarbon gas conversion process having substantially greater throughputs than the second process. The third system includes substantially the same components as the second system operating in substantially the same manner as the second process. The third system, however, reconfigures the two turbine/compressor sets such that the second turbine/compressor set substitutes an auxiliary primary compressor for the secondary compressor that is operable in cooperation with the primary compressor. The third system further provides an auxiliary secondary power turbine operable in cooperation with the secondary power turbine. The reconfigured and additional components are provided to compress a feed air to a primary air in two stages and to produce power for alternate power users external to the process in a manner described hereafter. The third process is performed by initially providing a feed to the third system comprising the feed air and a primary hydrocarbon gas divisible into a first portion and a second portion. The feed air is compressed in the auxiliary primary compressor to produce an intermediate air. The intermediate air is conveyed to the primary compressor and further compressed therein to produce the primary air divisible into a first portion and a second portion. The first portion of primary air is fed with the first portion of primary hydrocarbon gas, and optionally water or steam, to the combustion zone of the primary combustor, producing a primary combustion gas therein. The primary combustion gas is reacted with the second portion of primary hydrocarbon gas in the reforming zone of the primary combustor to produce a reformed gas that is rapidly expanded across the primary power turbine, thereby driving the primary power turbine and correspondingly driving the primary compressor.

The second portion of primary air is preheated by heat exchange with the reformed gas exiting the primary turbine to form a secondary air that is divided into a first portion and a second portion. The feed to the system further comprises a secondary hydrocarbon gas that is preheated by heat exchange with the reformed gas downstream of the air preheating step. The preheated secondary hydrocarbon gas is fed with the first portion of secondary air to the flame zone of the secondary combustor and combusted therein to produce a secondary combustion gas. The second portion of secondary air is fed with the secondary combustion gas, and optionally water or steam, to the burn-out zone of the secondary combustor to further oxidize the combustibles therein, while diluting and cooling the secondary combustion gas to suppress the formation of oxides of nitrogen in the burn-out zone. The resulting off-gas exiting the secondary combustor is expanded across the secondary power turbine.

In distinction to the second process, the secondary power turbine is connected by an auxiliary primary shaft to the auxiliary primary compressor, thereby driving the auxiliary primary compressor. The off-gas exiting the secondary power turbine is conveyed to the auxiliary secondary power turbine where it is further expanded before discharging the off-gas from the system. The shaft power from the secondary auxiliary turbine may be utilized for alternate power users external to the system, such as an electrical generator. After cooling the reformed gas by heat exchange with the second portion of primary air and the secondary hydrocarbon gas, the reformed gas is withdrawn from the system at a relatively low pressure for subsequent uses as desired.

The present system and process for conversion of a hydrocarbon gas to a reformed hydrogen-containing gas has been found to be more cost effective in each of its several embodiments relative to conventional hydrocarbon gas conversion systems because of reduced capital equipment and operating costs and improved product yields. Specifically, integration of a gas turbine cycle into the conversion system eliminates the high capital cost of providing electric or steam powered air compressors for compression of the air feed to the one or more combustor. The present system also has the practical advantage of enabling commercially available gas turbine engine packages to be utilized in the gas turbine cycle. Commercial gas turbine engine packages are available in many designs and sizes and are mass produced on a large scale to achieve a high degree of cost-effectiveness as well as rugged and reliable service.

The operating cost of the integral gas turbine cycle is substantially lower than the operating cost of externally-powered air compressors because the one or more gas turbines are driven by the reformed gas produced as an intermediate to the manufacture of desirable products such as liquid hydrocarbon fuels or petrochemicals. The injection of steam or water into the primary combustor also beneficially moderates temperatures and increases mass flow rates to the power turbines, thereby enabling the use of standard metallurgy in the power turbines without a substantial loss in thermal efficiency. The net effect of these enhancements is to maintain the capital cost of the system at relatively low levels.

The invention will be further understood from the accompanying drawings and description.

DESCRIPTION OF PREFERRED EMBODIMENTS

Figure 1:
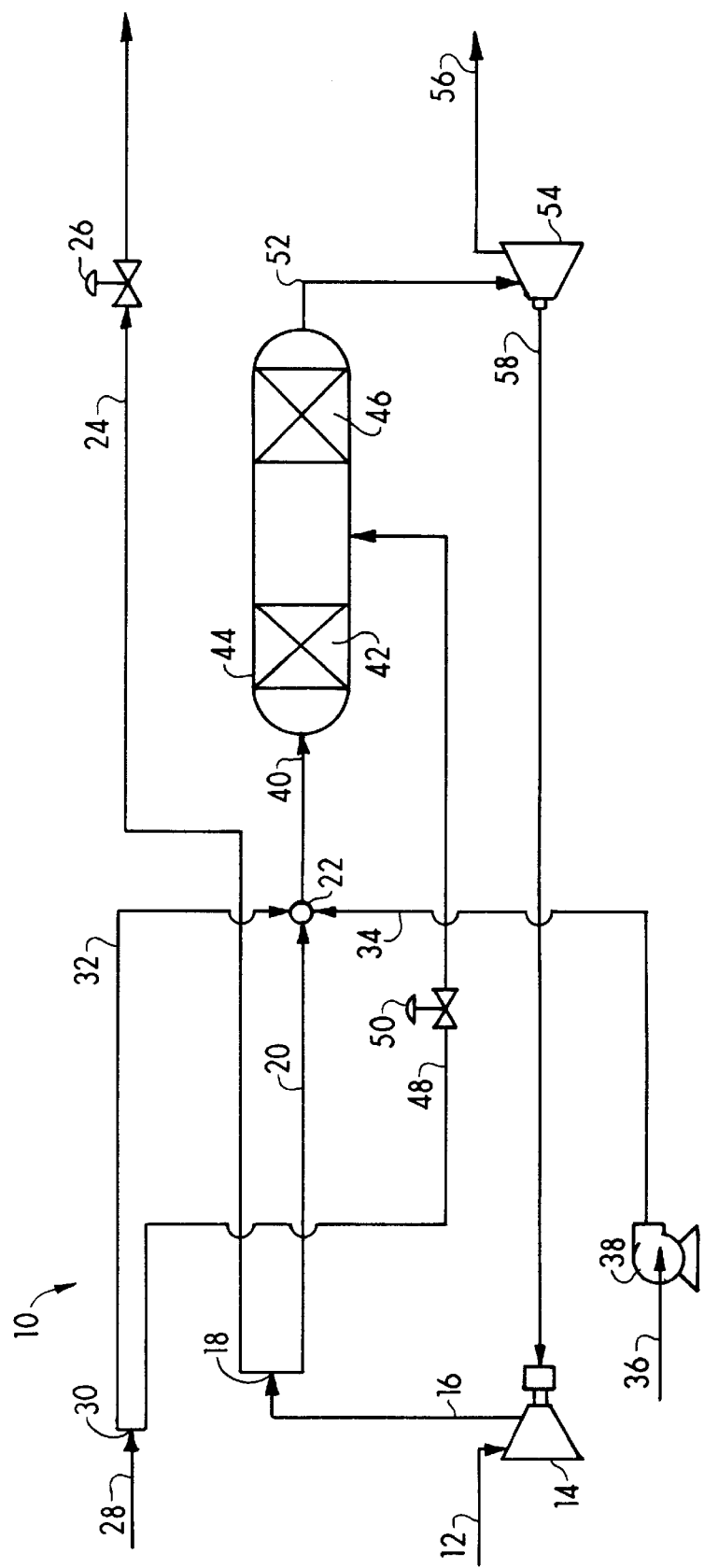
FIG. 1 is a schematic of a first embodiment of the system and process of the present invention.

The present invention relates to a hydrocarbon gas conversion process for producing a hydrogen-containing reformed gas. The invention further relates to a system of interconnected process equipment for practicing the hydrocarbon gas conversion process. An embodiment of a system and process of the present invention are initially described hereafter with reference to the FIG. 1, wherein the system is generally designated 10. The system 10 is characterized by the integration of a single gas turbine/compressor set therein as will be described hereafter. The system 10 demonstrates a preferred embodiment of an equipment configuration and a process practiced therewith for a relatively small-size application, wherein operating pressure conditions are compatible with commercially available gas turbine/compressor sets. It is apparent to the skilled artisan from the teaching herein, however, that the system 10 can be modified within the scope of the present invention for other size applications and operating conditions.

The system 10 has an air inlet 12 that delivers a feed air to a primary compressor 14 at a rate between about 5000 and about 5400 m$^3$/hr, a pressure between about 75 and about 150 kPa and a temperature between about −30° and about 40° C. The feed air is preferably air from the ambient atmosphere at ambient pressure and temperature conditions. The primary compressor 14 compresses the feed air to a primary air having a pressure between about 1000 and about 1050 kPa and a temperature between about 300° and about 350° C. The primary air is expelled from the primary compressor 14 to a primary air line 16 that feeds into a primary air manifold 18. The primary air is divided within the primary air manifold 18 into a first portion and a second portion. The first portion of primary air is the primary combustion air constituting the bulk of the total primary air. The primary combustion air is withdrawn from the primary air manifold 18 via a primary combustion air line 20 and fed to a primary burner mixer 22, such as a mixing manifold or other known mixing means. The second portion of primary air is a bleed air that is withdrawn from the primary air manifold 18 via a bleed air line 24 at a rate between about 1000 and about 1500 m$^3$/hr and discharged from the system 10 via a bleed air flow control valve 26 for alternate uses.

The system 10 further has a primary hydrocarbon gas inlet 28 that delivers a primary hydrocarbon gas to the system 10 from a remote source (not shown). The primary hydrocarbon gas is preferably a naturally-occurring, non-synthetic hydrocarbon gas produced from a subsurface formation. Among such gases, natural gas is most preferred, although other hydrocarbon gases have utility herein, including subquality gas containing nitrogen and/or carbon dioxide, gas derived from coal seams or gas derived from ocean hydrates. The primary hydrocarbon gas is received through the primary hydrocarbon gas inlet 28 at a rate between about 1000 and about 1200 m$^3$/hr, a pressure between about 1500 and about 2500 kPa, and a temperature between about 10° and about 50° C. It is noted that the flow rate of primary combustion air through the primary combustion air line 20 is substoichiometric relative to the flow rate of primary hydrocarbon gas through the primary hydrocarbon gas inlet 28. In particular, the primary combustion air contains only between about 35 and about 45% of the oxygen required for complete combustion of the primary hydrocarbon gas. The primary hydrocarbon gas inlet 28 feeds into a primary hydrocarbon gas manifold 30 that divides the primary hydrocarbon gas into a first portion and a second portion. The first portion of primary hydrocarbon gas is the primary burner gas constituting between about 25 and about 50% by volume of the total primary hydrocarbon gas. The first portion of primary hydrocarbon gas is fed via a primary burner gas line 32 to the primary burner mixer 22.

A primary water/steam line 34 also feeds into the primary burner mixer 22, optionally delivering either primary water or primary steam to the system 10 from a remote source (not shown). In the event the practitioner elects to convey primary water to the primary burner mixer 22, feed water is received into the system 10 at a rate between about 250 and about 1000 kg/hr via a primary water/steam inlet 36. The feed water is generally at a pressure between about 100 and about 300 kPa and a temperature between about 10° and about 50° C. The feed water is pressurized to primary water by means of an in-line pump 38 that displaces the primary water to the primary water/steam line 34. The primary water has a pressure between about 1500 and about 2500 kPa and a temperature between about 10° and about 50° C.

In the event the practitioner elects to convey primary steam to the primary burner mixer 22, substantially the same means of conveyance are applied to the steam as water. However, the in-line pump 38 is omitted from the system 10. The primary steam is fed directly to the primary burner mixer 22 via the primary water/steam line 34 at about the same rate and pressure as the primary water, but at a higher temperature between about 200° and about 250° C.

The primary combustion air, primary burner gas, and optionally primary water or primary steam are fully mixed in the primary burner mixer 22 to form a primary burner mixture, preferably having a molar composition of between about 70 and about 75% air, between about 5 and about 15% hydrocarbon gas, and between about 11 and about 28% steam or water, with the remainder being carbon dioxide and other trace compounds. The molar ratio of primary combustion air to primary burner gas in the primary burner mixture is near-stoichiometric, being between about 7.5:1 and about 12:1. The primary burner mixture preferably contains between about 20% deficient to about 20% excess of oxygen required for complete combustion of the hydrocarbons in the primary burner mixture. The primary burner mixture is fed directly from the primary burner mixer 22 to a primary burner assembly 40 where the primary burner mixture is ignited for combustion within a combustion zone 42 associated with the primary burner assembly 40. The primary burner mixture is at a pressure between about 1000 and about 1050 kPa and a temperature between about 95° and about 300° C. within the primary burner assembly 40 before being displaced into the combustion zone 42 at a rate between about 5000 and about 6000 m$^3$/hr.

The combustion zone 42 is one of two zones within a primary combustor 44, the other zone being a reforming zone 46 downstream of the combustion zone 42. The primary combustor 44 is a high temperature and high pressure continuous vessel typically maintained at a pressure between about 1000 and about 1500 kPa. The temperature in the combustion zone 42 is maintained between about 1200° and about 1700° C., enabling combustion of the primary burner mixture to a primary combustion gas. The primary combustion gas flows from the combustion zone 42 into the reforming zone 46.

The second portion of primary hydrocarbon gas, having been divided from the first portion of primary hydrocarbon gas in the primary hydrocarbon gas manifold 30, is a primary cooling gas constituting between about 50 and about 75% by volume of the total primary hydrocarbon gas. The second portion is injected via a primary cooling gas line 48, having a primary cooling gas flow control valve 50 positioned therein, into the reforming zone 46. The second portion of primary hydrocarbon gas fully mixes with the primary combustion gas forming a reforming mixture in the reforming zone 46. The reforming zone 46 may contain a catalyst to promote endothermic reforming reactions therein, but the primary combustor 44 preferably is substantially free of any catalysts insofar as catalysts are generally unnecessary for effective operation of the present system 10.

Substantial cooling of the reforming mixture occurs in the reforming zone 46 as the endothermic reforming reactions proceed, but the high temperature of the combustion zone 42 due to the near-stoichiometric composition of the primary burner mixture maintains the reforming mixture at a sufficiently high temperature to activate the ensuing endothermic reforming reactions and approach thermodynamic equilibrium in the reforming zone 46. Accordingly, significant conversion of the reforming mixture is achieved in the reforming zone 46 producing a reformed gas containing hydrogen and carbon monoxide in a desirable ratio. A representative molar composition of a desireable reformed gas is about 42% nitrogen, 26% hydrogen, 8% carbon monoxide, 6% carbon dioxide and 17% water.

The specific primary combustor conditions of temperature, pressure and quantitative composition can be selected within the above-recited ranges in accordance with the present teaching along with teaching known to the skilled artisan to achieve a predetermined ratio of hydrogen to carbon monoxide in the reformed gas as a function of the desired end use of the reformed gas. For example, if the desired end use of the reformed gas is as a synthesis gas for the production of hydrocarbon liquids or petrochemicals, the specific primary combustor conditions are selected such that the molar ratio of hydrogen to carbon monoxide in the reformed gas is between about 1.9:1 and about 2.2:1, and is preferably about 2:1. Alternatively, if the desired end use of the reformed gas is as a hydrogen-containing reducing gas for the reduction of metallurgical ore or the hydrogenation of heavy oils or coals, the specific primary combustor conditions are selected such that the molar ratio of hydrogen to carbon monoxide in the reformed gas is between about 1.8:1 and about 3.6:1, and is preferably at least about 3:1. It is further noted that the presence of water or steam in the combustion zone 42 desirably moderates the combustion temperature, reduces carbon/soot formation and augments hydrogen production by the water-gas shift reaction, thereby increasing the ratio of hydrogen to carbon monoxide.

The reformed gas is displaced from the reforming zone 46 of the primary combustor 44 and conveyed via a reformed gas line 52 to a primary power turbine 54 at a rate between about 7500 and about 8500 m$^3$/hr, a pressure between about 1000 and about 1050 kPa and a temperature between about 750° and about 1000° C. The reformed gas is partially expanded across the primary power turbine 54 and thereafter recovered for its desired end use from the primary power turbine 54 via a reformed gas outlet 56. The primary power turbine 54 is mechanically linked to the primary compressor 14 by means of a rotatable primary shaft 58, providing the power requirements to drive the primary compressor 14. It is apparent that the system 10 exhibits energy self-sufficiency to the extent power generated by expansion of the reformed gas exiting the primary combustor 44 is utilized to compress the air in the primary compressor 14 that is fed to the primary combustor 44. The system 10 also provides substantial quantities of excess high pressure bleed air that has utility in any number of alternate applications, including the combustion of waste gases generated by processes utilizing the reformed gas.

Figure 2:
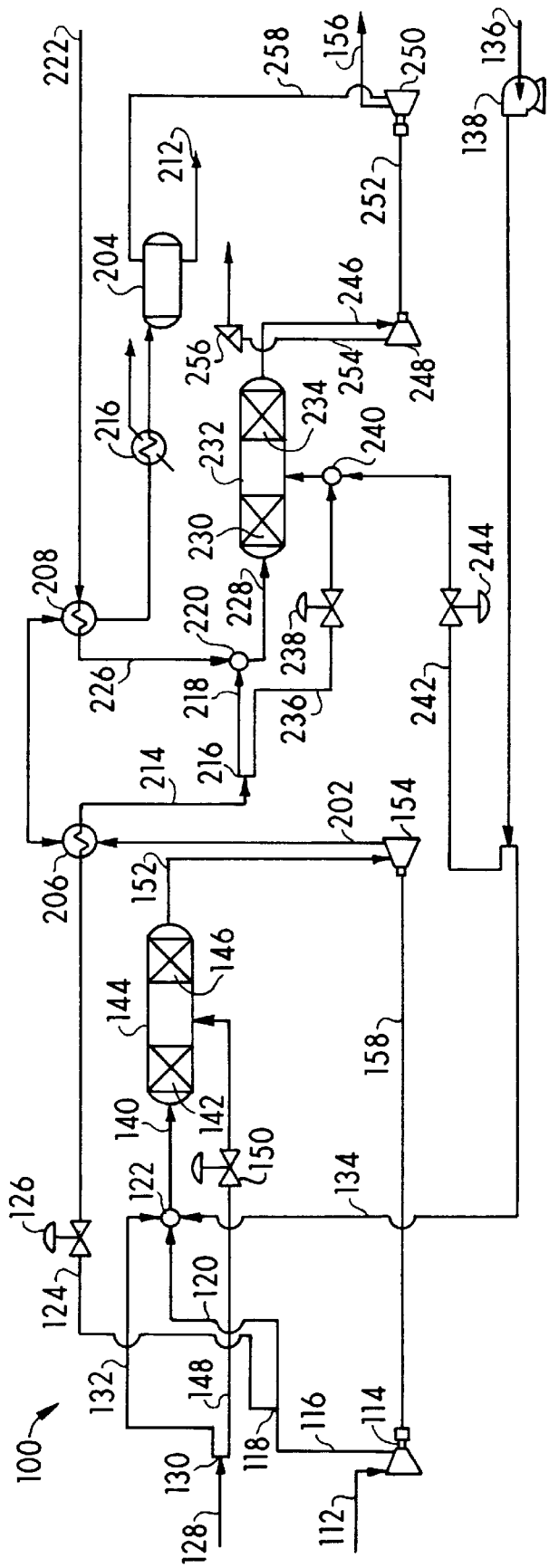
FIG. 2 is a schematic of an alternate second embodiment of the system and process of the present invention.

An alternate second embodiment of a second system and a second process of the present invention are described hereafter with reference to the FIG. 2, wherein the second system is generally designated 100. The second system 100 is substantially the same as the first system 10, however, the second system 100 further includes a second gas turbine/compressor set to process a secondary hydrocarbon gas stream, as will be described hereafter, in conjunction with the first gas turbine/compressor set processing the primary hydrocarbon gas stream. Components of the second system 100 corresponding to components of the first system 10 are designated by a three digit reference number, wherein the first digit of the reference number is one and the second two digits of the reference number are identical to the reference number of the corresponding first system component.

The system 100 has an air inlet 112 that delivers feed air to a primary compressor 114 at a rate between about 45,000 and about 55,000 m$^3$/hr, a pressure between about 75 and about 150 kPa and a temperature between about −30° and about 40° C. The feed air is preferably air from the ambient atmosphere at ambient pressure and temperature conditions. The primary compressor 114 compresses the feed air to a primary air having a pressure between about 900 and about 1100 kPa and a temperature between about 300° and about 350° C. The primary air is expelled from the primary compressor 114 to a primary air line 1 16 that feeds into a primary air manifold 118. The primary air is divided within the primary air manifold 118 into a first portion and a second portion. The first portion of primary air is a primary combustion air constituting the bulk of the total primary air. The primary combustion air is withdrawn from the primary air manifold 118 via a primary combustion air line 120 and fed to a primary burner mixer 122 at a rate between about 35,000 and about 40,000 m$^3$/hr. The second portion of primary air is a bleed air that is withdrawn from the primary air manifold 118 via a bleed air line 124 having a bleed air flow control valve 126 positioned therein. The volumetric ratio of primary combustion air to bleed air is between about 1:0.25 and about 1:0.5.

The system 100 further has a primary hydrocarbon gas inlet 128 that delivers a primary hydrocarbon gas to the system 100 from a remote source (not shown). The primary hydrocarbon gas is preferably a naturally-occurring, non-synthetic hydrocarbon gas produced from a subsurface formation, such as natural gas, subquality gas containing nitrogen and/or carbon dioxide, gas derived from coal seams or gas derived from ocean hydrates. The primary hydrocarbon gas is received through the primary hydrocarbon gas inlet 128 at a rate between about 11,000 and about 12,000 m$^3$/hr, a pressure between about 900 and about 1100 kPa, and a temperature between about 5° and about 40° C. It is noted that the flow rate of primary combustion air through the primary combustion air line 120 is substoichiometric relative to the flow rate of primary hydrocarbon gas through the primary hydrocarbon gas inlet 128. In particular, the primary combustion air contains only between about 35 and about 45% of the oxygen required for complete combustion of the primary hydrocarbon gas. The primary hydrocarbon gas inlet 128 feeds into a primary hydrocarbon gas manifold 130 that divides the primary hydrocarbon gas into a first portion and a second portion. The first portion of primary hydrocarbon gas is the primary burner gas constituting between about 25 and about 50% by volume of the total primary hydrocarbon gas. The first portion of primary hydrocarbon gas is fed via a primary burner gas line 132 to the primary burner mixer 122.

A primary water/steam line 134 also feeds into the primary burner mixer 122, optionally delivering either primary water or primary steam to the system 100 from a remote source (not shown). In the event the practitioner elects to convey primary water to the primary burner mixer 122, a feed water is received into the system 100 at a rate between about 6000 and about 7000 kg/hr via a water/steam inlet 136. The feed water is generally at a pressure between about 75 and about 150 kPa and a temperature between about 5° and about 50° C. The feed water is pressurized by means of an in-line pump 138 that displaces a first portion of the feed water as primary water to the primary water/steam line 134 at a rate between about 800 and about 1100 kg/hr, a pressure between about 1000 and about 2500 kPa, and a temperature between about 5° and about 50° C.

In the event the practitioner elects to convey primary steam to the primary burner mixer 122, substantially the same means of conveyance are applied to the steam as water. However, the in-line pump 138 is omitted from the system 100. The primary steam is fed directly to the primary burner mixer 122 via the primary water/steam line 134 at about the same rate and pressure as the primary water, but at a higher temperature between about 200° and about 250° C.

The primary combustion air, primary burner gas, and optionally primary water or primary steam are fully mixed in the primary burner mixer 122 to form a primary burner mixture, preferably having a molar composition of between about 85 and about 90% air, between about 5 and about 10% hydrocarbon gas, and between about 0 and about 5% steam or water, with the remainder being carbon dioxide and other trace compounds. The molar ratio of primary combustion air to primary burner gas in the primary burner mixture is near-stoichiometric being between about 7.5:1 and about 12:1. The primary burner mixture preferably contains between about 20% deficient to about 20% excess of oxygen required for complete combustion of the hydrocarbons in the primary burner mixture. The primary burner mixture is fed directly from the primary burner mixer 122 to a primary burner assembly 140 where the primary burner mixture is ignited for combustion within a combustion zone 142 associated with the primary burner assembly 140. The primary burner mixture is at a pressure between about 950 and about 1050 kPa and a temperature between about 150° and about 300° C. within the primary burner assembly 140 before being displaced into the combustion zone 142 at a rate between about 40,000 and about 50,000 m$^3$/hr.

The combustion zone 142 is one of two zones within a primary combustor 144, the other zone being a reforming zone 146 downstream of the combustion zone 142. The primary combustor 144 is a continuous vessel typically maintained at a pressure between about 850 and about 1000 kPa. The temperature in the combustion zone 142 is maintained between about 1700° and about 2000° C., enabling combustion of the primary burner mixture to a primary combustion gas therein.

The second portion of primary hydrocarbon gas, having been divided from the first portion of primary hydrocarbon gas in the primary hydrocarbon gas manifold 130, is a primary cooling gas constituting between about 50 and about 75% by volume of the total primary hydrocarbon gas. The second portion is injected via a primary cooling gas line 148, having a primary cooling gas flow control valve 150 positioned therein, into the primary combustor 144 downstream of the combustion zone 142 and upstream of the reforming zone 146. The second portion of primary hydrocarbon gas fully mixes with the primary combustion gas forming a reforming mixture that flows into the reforming zone 146. The reforming zone 146 may contain a catalyst to promote endothermic reforming reactions therein, but the primary combustor 144 preferably is substantially free of any catalysts insofar as catalysts are generally unnecessary for effective operation thereof.

Substantial cooling of the reforming mixture occurs in the reforming zone 146 as the endothermic reforming reactions proceed, but the high temperature of the combustion zone 142 due to the near-stoichiometric composition of the primary burner mixture maintains the reforming mixture at a sufficiently high temperature to activate the ensuing endothermic reforming reactions and to approach thermodynamic equilibrium in the reforming zone 146. Accordingly, significant conversion of the reforming mixture is achieved in the reforming zone 146 producing a reformed gas containing hydrogen and carbon monoxide in a desirable ratio. A representative molar composition of a desirable reformed gas is about 45% nitrogen, 30% hydrogen, 15% carbon monoxide, 3% carbon dioxide and 7% water and less than 1% hydrocarbon. The specific primary combustor conditions of temperature, pressure and quantitative composition can be selected within the above-recited ranges in accordance with the present teaching along with teaching known to the skilled artisan to achieve a predetermined ratio of hydrogen to carbon monoxide in the reformed gas as a function of the desired end use of the reformed gas.

The reformed gas is displaced from the reforming zone 146 of the primary combustor 144 and conveyed via a reformed gas line 152 to a primary power turbine 154 at a rate between about 60,000 and about 65,000 m$^3$/hr, a pressure between about 800 and about 1000 kPa and a temperature between about 850° and about 950° C. The reformed gas is partially expanded across the primary power turbine 154 that is mechanically linked to the primary compressor 114 by means of a rotatable primary shaft 158, providing the power requirements to drive the primary compressor 114. After partial expansion, the reformed gas is conveyed via a reformed gas cooling line 202 to a water separator 204. A series of heat exchangers 206, 208, 210 are positioned in the reformed gas cooling line 202 upstream of the water separator 204, operating in a manner described hereafter to cool the reformed gas to a temperature between about 40° and about 50° C. and a pressure between about 200 and about 300 kPa upon reaching the water separator 204. These conditions condense water in the reformed gas which is separated from the reformed gas in the water separator 204 and discharged from the system 100 via a water outlet line 212.

The bleed air is fed via the bleed air line 124 and the bleed air flow control valve 126 to the bleed air heat exchanger 206 where the reformed gas from the reformed gas cooling line 202 preheats the bleed air, forming a secondary air having a temperature between about 500° and about 600° C. and a pressure between about 250 and about 350 kPa. The reformed gas correspondingly exits the bleed air heat exchanger 206 at a temperature between about 550° and about 650° C. and a pressure between about 250 and about 300 kPa. The secondary air is fed via a secondary air line 214 to a secondary air manifold 216 where the secondary air is divided into a first portion and a second portion. The first portion of secondary air is the secondary flame air that is withdrawn from the secondary air manifold 216 via a secondary flame air line 218 and fed to a secondary burner mixer 220 at a rate between about 12,500 and about 13,500 m$^3$/hr.

The system 100 further has a secondary hydrocarbon gas inlet 222 that delivers a secondary hydrocarbon gas to the system 100 from a remote source (not shown). The secondary hydrocarbon gas is preferably a waste gas from an unassociated process that contains unconverted hydrogen and carbon monoxide and unrecoverable hydrocarbons. For example, the secondary hydrocarbon gas can be a gaseous waste product of a process utilizing the reformed gas of the present process. A representative molar composition of a desirable secondary hydrocarbon gas is in the range of between about 85 and about 90% nitrogen, about 1 and about 3% hydrogen, about 1 and about 3% carbon monoxide, about 4 and about 5% carbon dioxide, about 3% water, and about 1 and about 3% methane and other hydrocarbons. Typically the secondary hydrocarbon gas has a relatively low heating value, substantially lower than that of the primary hydrocarbon gas and containing only between about 4 and about 10% combustibles.

The secondary hydrocarbon gas is received through the secondary hydrocarbon gas inlet 222 at a rate between about 30,000 and about 35,000 m$^3$/hr, a pressure between about 300 and about 400 kPa, and a temperature between about 5° and about 50° C. The secondary hydrocarbon gas is fed via the secondary hydrocarbon gas inlet 222 into the secondary hydrocarbon gas heat exchanger 208, where the reformed gas from the reformed gas cooling line 202 preheats the secondary hydrocarbon gas to a temperature between about 300° and about 400° C. and a pressure between about 250 and about 350 kPa. The reformed gas correspondingly exits the secondary hydrocarbon gas heat exchanger 208 at a temperature between about 400° and about 500° C. and a pressure between about 250 and about 350 kPa. The secondary hydrocarbon gas is fed via a secondary hydrocarbon gas line 226 to the secondary burner mixer 220.

The secondary flame air and secondary hydrocarbon gas are fully mixed in the secondary burner mixer 220 to form a secondary burner mixture, preferably having a molar composition of between about 80 and about 90% nitrogen, between about 5 and about 10% oxygen, about 5% non-combustibles, and between about 3 and about 5% combustibles. As such the molar ratio of secondary flame air to secondary hydrocarbon gas in the secondary burner mixture is between about 0.3:1 and about 0.5:1. The secondary burner mixture is fed directly from the secondary burner mixer 220 to a secondary burner assembly 228 where the secondary burner mixture is ignited for combustion within a flame zone 230 associated with the secondary burner assembly 228. The secondary burner mixture is at a pressure between about 250 and about 350 kPa and a temperature between about 350° and about 450° C. within the secondary burner assembly 228 before being displaced into the flame zone 230 at a rate between about 40,000 and about 50,000 m³/hr.

The flame zone 230 is one of two zones within a secondary combustor 232, the other zone being an oxidation zone 234 downstream of the flame zone 230. The secondary combustor 232 is a continuous vessel typically maintained at a pressure between about 200 and about 300 kPa. The temperature in the flame zone 230 is maintained between about 1000° and about 1300° C., enabling combustion of the secondary burner mixture to a secondary combustion gas therein.

The second portion of secondary air, having been divided from the first portion of secondary air, is a secondary oxidation air that is withdrawn from the secondary air manifold 216 via a secondary oxidation air line 236, having a secondary oxidation air flow control valve 238 positioned therein, and fed to a secondary oxidation mixer 240. A secondary water/steam line 242, having a secondary water/steam flow control valve 244 positioned therein, diverts a second portion of the feed water or steam as secondary water or steam to the secondary oxidation mixer 240. The secondary water or steam is the quantity of feed water or steam remaining after removal of the primary water or steam therefrom via the primary water/steam 134 line. The secondary oxidation air and secondary water or steam are mixed in the secondary oxidation mixer 240 to form a secondary premix and injected into the secondary combustor 232 downstream of the flame zone 230 and upstream of the oxidation zone 234. The secondary premix fully mixes with the secondary combustion gas, forming an oxidation mixture that flows into the oxidation zone 234.

The temperature in the oxidation zone 234 is maintained between about 700° and about 1000° C. to fully oxidize the oxidation mixture, producing an off-gas that is withdrawn from the secondary combustor 232 at a rate between about 60,000 and about 65,000 kg/hr and fed into an off-gas outlet line 246 at a pressure between about 200 and about 250 kPa and a temperature between about 700° and about 1000° C. An exemplary off-gas has a molar composition of about 74% nitrogen, 20% water, 5% carbon dioxide 1% oxygen and traces of carbon monoxide and oxides of nitrogen. The secondary combustor 232 may be provided with a catalyst to promote the reactions therein, or may alternately be maintained substantially free of any catalysts. In any case, the operating parameters of the secondary combustor 232 are selected within the purview of the skilled artisan to substantially complete combustion of the gases fed thereto to carbon dioxide and water, while minimizing the formation of oxides of nitrogen and substantially completing oxidation of any organic contaminants contained in the feed water or steam entering the system 100 via the water/steam inlet 136.

The off-gas is conveyed via the off-gas outlet line 246 to a secondary power turbine 248 and expanded across it to drive the secondary power turbine 248. The secondary power turbine 248 is mechanically linked to a secondary compressor 250 by means of a rotatable secondary shaft 252, thereby providing the power requirements to correspondingly drive the secondary compressor 250. The expanded off-gas is withdrawn from the secondary power turbine 248 and conveyed via an exhaust line 254 to an exhaust flue 256 where the off-gas is discharged from the system 100 and preferably vented to the atmosphere at a pressure near atmospheric and a temperature between about 500° and about 600° C.

The reformed gas withdrawn from the water separator 204 is conveyed via a reformed gas suction line 258 to the secondary compressor 250 where it is compressed and thereafter recovered for its desired end use from the secondary compressor 250 via a reformed gas outlet 156. The reformed gas exits the system 100 via the reformed gas outlet at a pressure between about 700 and about 800 kPa and a temperature between about 150° and about 225° C.

Figure 3:
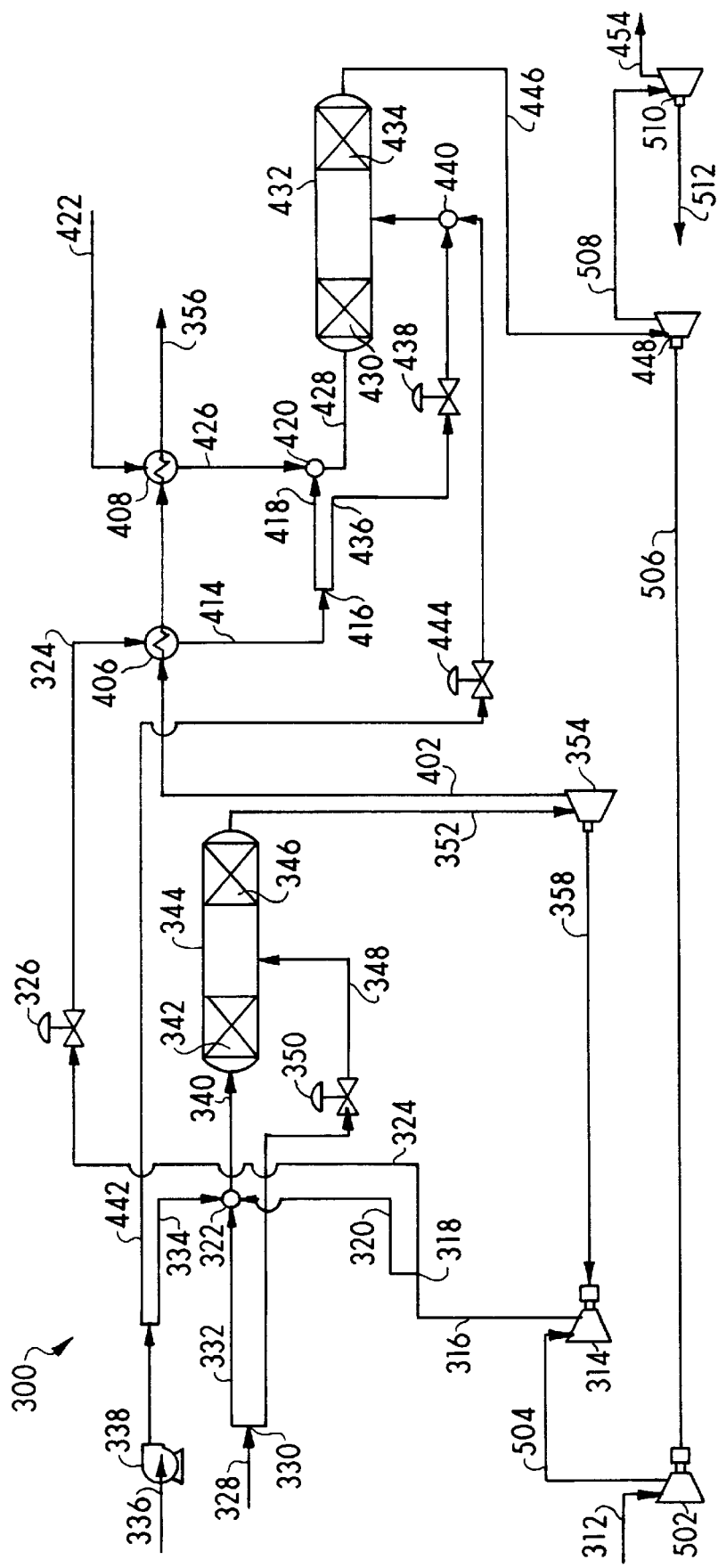
FIG. 3 is a schematic of an alternate third embodiment of the system and process of the present invention.

An alternate third embodiment of a third system and a third process of the present invention are described hereafter with reference to the FIG. 3, wherein the third system is generally designated 300. The third system 300 is substantially the same as the second system 100, however, the third system 300 modifies the configuration of the first and second gas turbine/compressor sets to jointly process the primary and secondary hydrocarbon gas streams, as will be described hereafter. Components of the third system 300 corresponding to components of the first system 10 are designated by a three digit reference number, wherein the first digit of the reference number is three and the second two digits of the reference number are identical to the reference number of the corresponding first system component. Components of the third system 300 corresponding to components of the second system 100 are designated by a three digit reference number, wherein the first digit of the reference number is four and the second two digits of the reference number are identical to the reference number of the corresponding second system component.

The system 300 has an air inlet 312 that delivers feed air to an auxiliary primary compressor 502 at a rate between about 350,000 and about 360,000 m³/hr, a pressure between about 75 and about 150 kPa and a temperature between about −30° and about 40° C. The feed air is preferably air from the ambient atmosphere at ambient pressure and temperature conditions. The auxiliary primary compressor 502 compresses the feed air to an intermediate air having a pressure between about 200 and about 300 kPa and a temperature between about 100° and about 150° C. The intermediate air is expelled from the auxiliary primary compressor 502 to an intermediate air line 504 that feeds into a primary compressor 314. The primary compressor 314 compresses the intermediate air to a primary air having a pressure between about 2500 and about 2600 kPa and a temperature between about 500° and about 550° C. The primary air is expelled from the primary compressor 314 to a primary air line 316 that feeds into a primary air manifold 318.

The primary air is divided within the primary air manifold 318 into a first portion and a second portion. The first portion of primary air is a primary combustion air constituting the bulk of the total primary air. The primary combustion air is withdrawn from the primary air manifold 318 via a primary combustion air line 320 and fed to a primary burner mixer 322 at a rate between about 255,000 and about 265,000 m³/hr. The second portion of primary air is a bleed air that is withdrawn from the primary air manifold 318 via a bleed air line 324 having a bleed air flow control valve 326 positioned therein. The volumetric ratio of primary combustion air to bleed air is between about 2:1 and about 3.3:1.

The system 300 further has a primary hydrocarbon gas inlet 328 that delivers a primary hydrocarbon gas to the system 300 from a remote source (not shown). The primary hydrocarbon gas is preferably a naturally-occurring, non-synthetic hydrocarbon gas produced from a subsurface formation, such as natural gas, subquality gas containing nitrogen and/or carbon dioxide, gas derived from coal seams or gas derived from ocean hydrates. The primary hydrocarbon gas is received through the primary hydrocarbon gas inlet 328 at a rate between about 75,000 and about 80,000 m³/hr, a pressure between about 2500 and about 2600 kPa, and a temperature between about 5° and about 40° C. It is noted that the flow rate of primary combustion air through the primary combustion air line 320 is substoichiometric relative to the flow rate of primary hydrocarbon gas through the primary hydrocarbon gas inlet 328. In particular, the primary combustion air contains only between about 35 and about 45% of the oxygen required for complete combustion of the primary hydrocarbon gas. The primary hydrocarbon gas inlet 328 feeds into a primary hydrocarbon gas manifold 330 that divides the primary hydrocarbon gas into a first portion and a second portion. The first portion of primary hydrocarbon gas is the primary burner gas constituting between about 25 and about 50% by volume of the total primary hydrocarbon gas. The first portion of primary hydrocarbon gas is fed via a primary burner gas line 332 to the primary burner mixer 322.

A primary water/steam line 334 also feeds into the primary burner mixer 322, optionally delivering either primary water or primary steam to the system 300 from a remote source (not shown). In the event the practitioner elects to convey primary water to the primary burner mixer 322, a feed water is received into the system 300 at a rate between about 10,000 and about 40,000 kg/hr via a water/steam inlet 336. The feed water is generally at a pressure between about 75 and about 150 kPa and a temperature between about 5° and about 50° C. The feed water is pressurized by means of an in-line pump 338 that displaces a first portion of the feed water as primary water to the primary water/steam line 334 at a rate between about 10,000 and about 13,000 kg/hr, a pressure between about 2500 and about 3000 kPa, and a temperature between about 5° and about 50° C.

In the event the practitioner elects to convey primary steam to the primary burner mixer 322, substantially the same means of conveyance are applied to the steam as water. However, the in-line pump 338 is omitted from the system 300. The primary steam is fed directly to the primary burner mixer 322 via the primary water/steam line 334 at about the same rate as the primary water, but at a pressure between about 1500 and about 2500 kPa and a temperature between about 200° and about 250° C.

The primary combustion air, primary burner gas, and optionally primary water or primary steam are fully mixed in the primary burner mixer 322 to form a primary burner mixture, preferably having a molar composition of between about 85 and about 90% air, between about 5 and about 10% hydrocarbon gas, and between about 0 and about 5% steam or water, with the remainder being carbon dioxide and other trace compounds. The molar ratio of primary combustion air to primary burner gas in the primary burner mixture is near-stoichiometric, being between about 7.5:1 and about 12:1. The primary burner mixture preferably contains between about 20% deficient to about 20% excess of oxygen required for complete combustion of the hydrocarbons in the primary burner mixture. The primary burner mixture is fed directly from the primary burner mixer 322 to a primary burner assembly 340 where the primary burner mixture is ignited for combustion within a combustion zone 342 associated with the primary burner assembly 340. The primary burner mixture is at a pressure between about 2500 and about 3000 kPa and a temperature between about 300° and about 400° C. within the primary burner assembly 340 before being displaced into the combustion zone 342 at a rate between about 250,000 and about 350,000 m³/hr.

The combustion zone 342 is one of two zones within a primary combustor 344, the other zone being a reforming zone 346 downstream of the combustion zone 342. The primary combustor 344 is a continuous vessel typically maintained at a pressure between about 2500 and about 2100 kPa. The temperature in the combustion zone 342 is maintained between about 1200° and about 2100° C., enabling combustion of the primary burner mixture to a primary combustion gas therein.

The second portion of primary hydrocarbon gas, having been divided from the first portion of primary hydrocarbon gas in the primary hydrocarbon gas manifold 330, is a primary cooling gas constituting between about 50 and about 75% by volume of the total primary hydrocarbon gas. The second portion is injected via a primary cooling gas line 348, having a primary cooling gas flow control valve 350 positioned therein, into the primary combustor 344 downstream of the combustion zone 342 and upstream of the reforming zone 346. The second portion of primary hydrocarbon gas fully mixes with the primary combustion gas forming a reforming mixture that flows into the reforming zone 346. The reforming zone 346 may contain a catalyst to promote endothermic reforming reactions therein, but the primary combustor 344 preferably is substantially free of any catalysts insofar as catalysts are generally unnecessary for effective operation thereof.

Substantial cooling of the reforming mixture occurs in the reforming zone 346 as the endothermic reforming reactions proceed, but the high temperature of the combustion zone 342 due to the near-stoichiometric composition of the primary burner mixture maintains the reforming mixture at a sufficiently high temperature to activate the ensuing endothermic reforming reactions and to approach thermodynamic equilibrium in the reforming zone 346. Accordingly, significant conversion of the reforming mixture is achieved in the reforming zone 346 producing a reformed gas containing hydrogen and carbon monoxide in a desirable ratio. A representative molar composition of a desirable reformed gas is about 45% nitrogen, 30% hydrogen, 15% carbon monoxide, 3% carbon dioxide and 7% water and less than 1% hydrocarbon. The specific primary combustor conditions of temperature, pressure and quantitative composition can be selected within the above-recited ranges in accordance with the present teaching along with teaching known to the skilled artisan to achieve a predetermined ratio of hydrogen to carbon monoxide in the reformed gas as a function of the desired end use of the reformed gas.

The reformed gas is displaced from the reforming zone 346 of the primary combustor 344 and conveyed via a reformed gas line 352 to a primary power turbine 354 at a rate between about 400,000 and about 500,000 m³l/hr, a pressure between about 2500 and about 3000 kPa and a temperature between about 900° and about 1000° C. The reformed gas is partially expanded across the primary power turbine 354 that is mechanically linked to the primary compressor 314 by means of a rotatable primary shaft 358, providing the power requirements to drive the primary compressor 314. After partial expansion, the reformed gas is conveyed via a reformed gas cooling line 402 through a of pair heat exchangers 406 and 408 operating in a manner described hereafter to cool the reformed gas to a temperature between about 400° and about 550° C. and a pressure between about 500 and about 600 kPa. The reformed gas is recovered thereafter for its desired end use via a reformed gas outlet 356.

The bleed air is fed via the bleed air line 324 and the bleed air flow control valve 326 to the bleed air heat exchanger 406 where the reformed gas from the reformed gas cooling line 402 preheats the bleed air, forming a secondary air having a temperature between about 500° and about 600° C. and a pressure between about 200 and about 300 kPa. The reformed gas correspondingly exits the bleed air heat exchanger 406 at a temperature between about 650° and about 700° C. and a pressure between about 600 and about 650 kPa. The secondary air is fed via a secondary air line 414 to a secondary air manifold 416 where the secondary air is divided into a first portion and a second portion. The first portion of secondary air is the secondary flame air that is withdrawn from the secondary air manifold 416 via a secondary flame air line 418 and fed to a secondary burner mixer 420 at a rate between about 80,000 and about 85,000 m$^3$/hr.

The system 300 further has a secondary hydrocarbon gas inlet 422 that delivers a secondary hydrocarbon gas to the system 300 from a remote source (not shown). The secondary hydrocarbon gas is preferably a waste gas from an unassociated process that contains unconverted hydrogen and carbon monoxide and unrecoverable hydrocarbons. For example, the secondary hydrocarbon gas can be a gaseous waste product of a process utilizing the reformed gas of the present process. A representative molar composition of a desirable secondary hydrocarbon gas is in the range of between about 85 and about 90% nitrogen, about 1 and about 3% hydrogen, about 1 and about 3% carbon monoxide, about 4 and about 5% carbon dioxide, about 3% water, and about 1 and about 3% methane and other hydrocarbons. Typically the secondary hydrocarbon gas has a relatively low heating value, substantially lower than that of the primary hydrocarbon gas and containing only between about 4 and about 10% combustibles.

The secondary hydrocarbon gas is received through the secondary hydrocarbon gas inlet 422 at a rate between about 225,000 and about 250,000 m$^3$/hr, a pressure between about 200 and about 300 kPa, and a temperature between about 5° and about 50° C. The secondary hydrocarbon gas is fed via the secondary hydrocarbon gas inlet 422 into the secondary hydrocarbon gas heat exchanger 408, where the reformed gas from the reformed gas cooling line 402 preheats the secondary hydrocarbon gas to a temperature between about 300° and about 400° C. and a pressure between about 200 and about 300 kPa. The reformed gas correspondingly exits the secondary hydrocarbon gas heat exchanger 408 at a temperature between about 450° and about 550° C. and a pressure between about 500 and about 600 kPa. The secondary hydrocarbon gas is fed via a secondary hydrocarbon gas line 426 to the secondary burner mixer 420.

The secondary flame air and secondary hydrocarbon gas are fully mixed in the secondary burner mixer 420 to form a secondary burner mixture, preferably having a molar composition of between about 80 and about 90% nitrogen, between about 5 and about 10% oxygen, about 5% non-combustibles, and between about 3 and about 5% combustibles. As such the molar ratio of secondary flame air to secondary hydrocarbon gas in the secondary burner mixture is between about 0.3:1 and about 0.5:1. The secondary burner mixture is fed directly from the secondary burner mixer 420 to a secondary burner assembly 428 where the secondary burner mixture is ignited for combustion within a flame zone 430 associated with the secondary burner assembly 428. The secondary burner mixture is at a pressure between about 200 and about 300 kPa and a temperature between about 350° and about 450° C. within the secondary burner assembly 428 before being displaced into the flame zone 430 at a rate between about 300,000 and about 350,000 m$^3$/hr.

The flame zone 430 is one of two zones within a secondary combustor 432, the other zone being an oxidation zone 434 downstream of the flame zone 430. The secondary combustor 432 is a continuous vessel typically maintained at a pressure between about 150 and about 250 kPa. The temperature in the flame zone 430 is maintained between about 950° and about 1300° C., enabling combustion of the secondary burner mixture to a secondary combustion gas therein.

The second portion of secondary air, having been divided from the first portion of secondary air, is a secondary oxidation air that is withdrawn from the secondary air manifold 416 via a secondary oxidation air line 436, having a secondary oxidation air flow control valve 438 positioned therein, and fed to a secondary oxidation mixer 440. A secondary water/steam line 442, having a secondary water/steam flow control valve 444 positioned therein, diverts a second portion of the feed water or steam as secondary water or steam to the secondary oxidation mixer 440. The secondary water or steam is the quantity of feed water or steam remaining after removal of the primary water or steam therefrom via the primary water/steam 334 line. The secondary oxidation air and secondary water or steam are mixed in the secondary oxidation mixer 440 to form a secondary premix and injected into the secondary combustor 432 downstream of the flame zone 430 and upstream of the oxidation zone 434. The secondary premix fully mixes with the secondary combustion gas, forming an oxidation mixture that flows into the oxidation zone 434.

The temperature in the oxidation zone 434 is maintained between about 700° and about 1000° C. to fully oxidize the oxidation mixture, producing an off-gas that is withdrawn from the secondary combustor 432 at a rate between about 400,000 and about 450,000 kg/hr and fed into an off-gas outlet line 446 at a pressure between about 150 and about 250 kPa and a temperature between about 700° and about 1000° C. An exemplary off-gas has a molar composition of about 78% nitrogen, 16% water, 5% carbon dioxide, 1% oxygen and traces of carbon monoxide and oxides of nitrogen. The secondary combustor 432 may be provided with a catalyst to promote the reactions therein, or may alternately be maintained substantially free of any catalysts. In any case, the operating parameters of the secondary combustor 432 are selected within the purview of the skilled artisan to substantially complete combustion of the gases fed thereto to carbon dioxide and water, while minimizing the formation of oxides of nitrogen and substantially completing oxidation of any organic contaminants contained in the feed water or steam entering the system 300 via the water/steam inlet 336.

The off-gas is conveyed via the off-gas outlet line 446 to a secondary power turbine 448 and partially expanded across it to drive the secondary power turbine 448. The secondary power turbine 448 is mechanically linked to the auxiliary primary compressor 502 by means of a rotatable auxiliary primary shaft 506, thereby providing the power requirements to correspondingly drive the auxiliary primary compressor 502. The partially expanded off-gas is withdrawn from the secondary power turbine 448 at a rate between about 400,000 and about 500,000 kg/hr and conveyed via an off-gas auxiliary line 508 to an auxiliary secondary power turbine 510 at a pressure between about 100 and about 200 kPa and a temperature between about 600° and about 9000° C. The off-gas is further expanded across the auxiliary secondary power turbine 510 and thereafter discharged from the system 300 via an exhaust line 454 that preferably vents to the atmosphere. The auxiliary secondary power turbine 510 has an auxiliary secondary shaft 512 for providing power to an alternate power user (not shown) such as an electrical generator.

It is apparent to the skilled artisan that many alternatives are available within the scope of the present invention for selecting specific components having utility in the integrated gas turbine/compressor sets described herein. In particular, it is most practical to exploit and utilize commercially available gas-turbine engine packages. Commercial gas-turbine engine packages are commonly used to generate electric power or to drive industrial compressors or pumps. Commercial gas-turbine engine packages are also used for motive applications such as powering ships. As such, commercial packages are available in many designs and sizes. It is advantageous to select a package design and size that most closely matches the particular requirements of the given application. Thus, in the systems 10, 100 and 300, the size of the gas-turbine packages is preferably selected based on the volume of gas available for conversion to products. It is also noted that different designs of commercial gas-turbine engine packages operate at significantly different pressures and efficiencies. Accordingly, it is advantageous to select process pressure conditions that best utilize a particular gas-turbine package size and design.

While the foregoing preferred embodiments of the invention have been described and shown, it is understood that alternatives and modifications, such as those suggested and others, may be made thereto and fall within the scope of the present invention.

I claim:

1. A process for reforming a hydrocarbon gas comprising:
    a) providing a primary hydrocarbon gas divided into a first portion and a second portion and feeding a primary air and said first portion of said primary hydrocarbon gas to a combustion zone of a primary combustor having a reforming zone downstream of said combustion zone;
    b) combusting said primary air and said first portion of said primary hydrocarbon gas in said combustion zone to produce a primary combustion gas:
    c) feeding said primary combustion gas and said second portion of said primary hydrocarbon gas to said reforming zone and reacting said primary combustion gas therein to produce a reformed gas containing hydrogen and carbon monoxide;
    d) driving a primary power turbine with said reformed gas;
    e) driving a primary compressor with said primary power turbine; and
    f) compressing a feed air in said primary compressor to produce said primary air.

2. The process of claim 1 further comprising feeding water or steam to said combustion zone.

3. The process of claim 1 further comprising dividing said primary air produced from said feed air into a first portion and a second portion and wherein said primary air fed to said combustion zone is said first portion of said primary air.

4. The process of claim 3 further comprising feeding a secondary hydrocarbon gas and said second portion of said primary air as a secondary air to a secondary combustor and reacting said secondary hydrocarbon gas and said secondary air in said secondary combustor to produce an off-gas containing carbon dioxide and water.

5. The process of claim 4 further comprising driving a secondary power turbine with said off-gas.

6. The process of claim 5 further comprising driving a secondary compressor with said secondary power turbine.

7. The process of claim 5 further comprising driving an auxiliary primary compressor with said secondary power turbine to compress said feed air upstream of said primary compressor.

8. The process of claim 5 further comprising driving an auxiliary secondary power turbine with said off-gas after driving said secondary power turbine.

9. The process of claim 4 wherein said secondary combustor has a flame zone and an oxidation zone downstream of said flame zone and further wherein said secondary air and said secondary hydrocarbon gas are combusted in said flame zone to produce a secondary combustion gas.

10. The process of claim 9 further comprising dividing said secondary air into a first portion and a second portion and wherein said secondary air fed to said flame zone is said first portion of said secondary air.

11. The process of claim 10 further comprising feeding said second portion of said secondary air to said secondary combustor downstream of said flame zone and reacting said second portion of said secondary air with said secondary combustion gas in said oxidation zone to produce said off-gas.

12. A process for reforming a hydrocarbon gas comprising:
    a) compressing a feed air in a primary compressor to produce a primary air;
    b) dividing said primary air into a first portion and a second portion and dividing a primary hydrocarbon into a first portion and a second portion;
    c) combusting said first portion of said primary air and said first portion of said primary hydrocarbon gas in a combustion zone of a primary combustor having a reforming zone downstream of said combustion zone to produce a primary combustion gas;
    d) feeding said primary combustion gas and said second portion of said primary hydrocarbon gas to said reforming zone and reacting said primary combustion gas therein to produce a reformed gas containing hydrogen and carbon monoxide;
    e) driving a primary power turbine with said reformed gas;
    f) driving said primary compressor with said primary power turbine;
    g) feeding said second portion of said primary air as a secondary air to a secondary combustor with a secondary hydrocarbon gas;
    h) reacting said secondary hydrocarbon gas and said secondary air in said secondary combustor to produce an off-gas containing carbon dioxide and water;
    i) driving a secondary power turbine with said off-gas; and
    j) driving a secondary compressor with said secondary power turbine.

13. The process of claim 12 further comprising feeding water or steam to said combustion zone.

14. The process of claim 12 wherein said secondary combustor has a flame zone and an oxidation zone downstream of said flame zone and further wherein said secondary air and said secondary hydrocarbon gas are combusted in said flame zone to produce a secondary combustion gas.

15. The process of claim 14 further comprising dividing said secondary air into a first portion and a second portion and wherein said secondary air fed to said flame zone is said first portion of said secondary air.

16. The process of claim 15 further comprising feeding said second portion of said secondary air to said secondary combustor downstream of said flame zone and reacting said second portion of said secondary air with said secondary combustion gas in said oxidation zone to produce said off-gas.

17. A process for reforming a hydrocarbon gas comprising:
   a) compressing a feed air in an auxiliary primary compressor to produce an intermediate air;
   b) compressing said intermediate air in a primary compressor to produce a primary air;
   c) dividing said primary air into a first portion and a second portion and dividing a primary hydrocarbon into a first portion and a second portion;
   d) combusting said first portion of said primary air and said first portion of said primary hydrocarbon gas in a combustion zone of a primary combustor having a reforming zone downstream of said combustion zone to produce a primary combustion gas;
   e) feeding said primary combustion gas and said second portion of said primary hydrocarbon gas to said reforming zone and reacting said primary combustion gas therein to produce a reformed gas containing hydrogen and carbon monoxide;
   f) driving a primary power turbine with said reformed gas;
   g) driving said primary compressor with said primary power turbine;
   h) feeding said second portion of said primary air as a secondary air to a secondary combustor with a secondary hydrocarbon gas;
   i) reacting said secondary hydrocarbon gas and said secondary air in said secondary combustor to produce an off-gas containing carbon dioxide and water;
   j) driving a secondary power turbine with said off-gas; and
   k) driving said auxiliary primary compressor with said secondary power turbine.

18. The process of claim 17 further comprising feeding water or steam to said combustion zone.

19. The process of claim 17 wherein said secondary combustor has a flame zone and an oxidation zone downstream of said flame zone and further wherein said secondary air and said secondary hydrocarbon gas are combusted in said flame zone to produce a secondary combustion gas.

20. The process of claim 19 further comprising dividing said secondary air into a first portion and a second portion and wherein said secondary air fed to said flame zone is said first portion of said secondary air.

21. The process of claim 20 further comprising feeding said second portion of said secondary air to said secondary combustor downstream of said flame zone and reacting said second portion of said secondary air with said secondary combustion gas in said oxidation zone to produce said off-gas.

22. The process of claim 17 further comprising driving an auxiliary secondary power turbine with said off-gas after driving said secondary power turbine.

23. The process of claim 1 wherein said primary air fed to said combustion zone contains an amount of oxygen which is substantially stoichiometric for combustion of the hydrocarbons in said first portion of said primary hydrocarbon gas fed to said combustion zone.

24. The process of claim 1 wherein said primary air fed to said combustion zone contains an amount of oxygen which is between about 20% deficient to about 20% excess of the amount of oxygen required for substantially complete combustion of the hydrocarbons in said first portion of said primary hydrocarbon gas fed to said combustion zone.

25. The process of claim 1 wherein said primary combustor is substantially free of a catalyst for promoting reforming reactions in said primary combustor.

26. The process of claim 12 wherein said primary air fed to said combustion zone contains an amount of oxygen which is substantially stoichiometric for combustion of the hydrocarbons in said first portion of said primary hydrocarbon gas fed to said combustion zone.

27. The process of claim 12 wherein said primary air fed to said combustion zone contains an amount of oxygen which is between about 20% deficient to about 20% excess of the amount of oxygen required for substantially complete combustion of the hydrocarbons in said first portion of said primary hydrocarbon gas fed to said combustion zone.

28. The process of claim 12 wherein said primary combustor is substantially free of a catalyst for promoting reforming reactions in said primary combustor.

29. The process of claim 17 wherein said primary air fed to said combustion zone contains an amount of oxygen which is substantially stoichiometric for combustion of the hydrocarbons in said first portion of said primary hydrocarbon gas fed to said combustion zone.

30. The process of claim 17 wherein said primary air fed to said combustion zone contains an amount of oxygen which is between about 20% deficient to about 20% excess of the amount of oxygen required for substantially complete combustion of the hydrocarbons in said first portion of said primary hydrocarbon gas fed to said combustion zone.

31. The process of claim 17 wherein said primary combustor is substantially free of a catalyst for promoting reforming reactions in said primary combustor.

* * * * *

UNITED STATES PATENT AND TRADEMARK OFFICE
CERTIFICATE OF CORRECTION

PATENT NO. : 5,861,441
DATED : January 19, 1999
INVENTOR(S) : John J. Waycuilis

It is certified that error appears in the above-indentified patent and that said Letters Patent is hereby corrected as shown below:

Col. 9, line 62 : Delete "1 16" and insert --116--.
Col. 19, line 9 : Delete "9000" and insert --900--.

Signed and Sealed this

First Day of June, 1999

Attest:

Attesting Officer

Q. TODD DICKINSON

Acting Commissioner of Patents and Trademarks